US012778410B2

(12) United States Patent
Marin et al.

(10) Patent No.: US 12,778,410 B2
(45) Date of Patent: Nov. 3, 2026

(54) DEVICE AND A COMPUTER-IMPLEMENTED METHOD FOR DETERMINING A PARAMETER REPRESENTATIVE OF A VISUAL ACUITY

(71) Applicant: Essilor International, Charenton-le-Pont (FR)

(72) Inventors: Gildas Marin, Paris (FR); Stéphane Perrot, Saint Maur des Fosses (FR); Fabien Moreau, Paris (FR)

(73) Assignee: Essilor International, Charenton-le-Pont (FR)

(*) Notice: Subject to any disclaimer, the term of this patent is extended or adjusted under 35 U.S.C. 154(b) by 289 days.

(21) Appl. No.: 18/293,278

(22) PCT Filed: Jun. 30, 2022

(86) PCT No.: PCT/EP2022/068136
§ 371 (c)(1),
(2) Date: Jan. 29, 2024

(87) PCT Pub. No.: WO2023/006333
PCT Pub. Date: Feb. 2, 2023

(65) Prior Publication Data
US 2024/0374132 A1 Nov. 14, 2024

(30) Foreign Application Priority Data
Jul. 30, 2021 (EP) .................................... 21306064

(51) Int. Cl.
*A61B 3/028* (2006.01)
*A61B 3/06* (2006.01)

(52) U.S. Cl.
CPC .............. *A61B 3/028* (2013.01); *A61B 3/063* (2013.01)

(58) Field of Classification Search
CPC ................................ A61B 3/028; A61B 3/063
(Continued)

(56) References Cited

U.S. PATENT DOCUMENTS

2001/0043163 A1* 11/2001 Waldern ............ G02B 27/0093 345/7
2020/0214559 A1* 7/2020 Krueger ................ A61B 5/163
(Continued)

FOREIGN PATENT DOCUMENTS

JP 2003-93344 A 4/2003
JP 2003093344 A * 4/2003
(Continued)

OTHER PUBLICATIONS

International Search Report and Written Opinion issued Oct. 10, 2022 in PCT/EP2022/068136 filed on Jun. 30, 2022, 19 pages.

*Primary Examiner* — Bumsuk Won
*Assistant Examiner* — Mitchell T Oestreich
(74) *Attorney, Agent, or Firm* — Oblon, McClelland, Maier & Neustadt, L.L.P.

(57) ABSTRACT

A wearable device for determining a parameter representative of a visual acuity of a user, including a displaying unit configured to display at least one image to at least one eye of the user when the device is worn by the user, an optical unit disposed between the displaying unit and at least one eye of the user when the device is worn by the user, a diffuser disposed between the optical unit and at least one eye of the user when the device is worn by the user so that the diffuser faces at least one eye of the user, at least one light source for stimulating at least one eye of the user, and a sensing unit configured to acquire at least one signal representative of a visual acuity of the user.

19 Claims, 3 Drawing Sheets

(58) Field of Classification Search
USPC ........................................................ 351/243
See application file for complete search history.

(56) References Cited

U.S. PATENT DOCUMENTS

| | | | |
|---|---|---|---|
| 2021/0393122 | A1 | 12/2021 | Milea et al. |
| 2022/0022743 | A1 | 1/2022 | Munger et al. |
| 2022/0151489 | A1 | 5/2022 | Khan et al. |

FOREIGN PATENT DOCUMENTS

| | | | |
|---|---|---|---|
| JP | 3898095 | B2 | 3/2007 |
| WO | WO 2020/113347 | A1 | 6/2020 |
| WO | WO 2020/176784 | A1 | 9/2020 |
| WO | WO 2021/022028 | A1 | 2/2021 |
| WO | WO 2021/048509 | A1 | 3/2021 |
| WO | WO 2018/203828 | A1 | 11/2021 |

* cited by examiner

DEVICE AND A COMPUTER-IMPLEMENTED METHOD FOR DETERMINING A PARAMETER REPRESENTATIVE OF A VISUAL ACUITY

CROSS-REFERENCE TO RELATED APPLICATION(S)

The present application is a national stage application of PCT Application No. PCT/EP2022/068136, filed Jun. 30, 2022, which claims priority to European Patent Application No. 21306064.3, filed Jul. 30, 2021. The benefit of priority is claimed to each of the foregoing, and the entire contents of each of the foregoing are incorporated herein by reference.

FIELD OF THE INVENTION

The invention relates to the field of determining a parameter representative of a visual acuity, for example visual acuity recovering of a user after being exposed to a given light environment. Particularly, the invention is directed to a device for determining a parameter representative of a visual acuity. The invention further concerns a computer-implemented method for determining a parameter representative of a visual acuity.

BACKGROUND OF THE INVENTION

It is common in the art to determine light sensitivity of a user, notably for prescribing the most appropriate tinted lenses to the user. The user's light sensitivity may be measured by exposing the subject to glare or light possessing significant intensity.

An example of such a measuring device is disclosed in EP 3 752 046 wherein a wearable measurement device is able to provide the user with a homogeneous light diffusion to determine a light sensitivity threshold.

Then, we know that visual performances are decreased after being dazzled during a glare measurement. Visual acuity of the user is restored after a given recovery time. The knowledge of the evolution of this vision recovery time can notably improve the accuracy of light sensitivity measurement. Such a visual acuity recovery is determined by displaying to the user a visual shape, e.g. an optotype. Visual acuity is considered to be recovered when said visual shape is recognized by the user. An example of such an optotype is a C-shaped optotype wherein the gap between the two ends of the C is randomly oriented in a given direction. In this measurement test, the user has to determine the right orientation of the optotype.

To respect the standards (see for example ISO standards 8596 and 8597), the optotype has to be displayed to the user with a predetermined resolution to assess the measurement (e.g. 5/10).

Measuring systems involving several devices able to first expose the user to glare and then measure visual acuity recovery time exist but have significant bulkiness and heaviness that requires to dispose this system on a support, as a table. Therefore, this interactive testing system is difficult to move so that it is intended to be stationary. This may render the measurement of the subject's visual acuity recovery time laborious and not practical.

Known wearable measurement devices as in EP 3 752 046 are not configured to measure visual acuity recovery time. Furthermore, this wearable measurement device comprises a large diffuser which is positioned near and is oriented toward the user's face. Indeed, the diffuser forms a physical obstacle which makes it very difficult to also be able to measure visual acuity recovery time. The integration of a visual acuity measurement system is thus rendered very difficult while maintaining the homogeneity of the light emission and be able to display an optotype or any scene/picture having the right resolution.

A problem that the invention aims to solve is thus to provide a device configured to provide sufficient light homogeneity for measuring light sensitivity threshold of a user while allowing to correctly measure a parameter representative of the visual acuity of said user after or during exposure to a given light environment.

SUMMARY OF THE INVENTION

To that end, the invention provides a device for determining a parameter representative of a visual acuity of a user, comprising:

- a displaying unit configured to display at least one image to at least one eye of the user when the device is worn by the user,
- an optical unit disposed between the displaying unit and at least one eye of the user when the device is worn by the user,
- a diffuser disposed between said optical unit and at least one eye of the user when the device is worn by the user so that said diffuser faces at least one eye of the user,
- at least one light source for stimulating at least one eye of the user,
- a sensing unit configured to acquire at least one signal representative of a visual acuity of the user
- means allowing said user to see said displaying unit through said optical unit despite the disposition of the diffuser between said optical unit and at least one eye of the user when the device is worn by the user.

The arrangement of said device allows to perform visual acuity measurement while positioning the diffuser to be configured to provide sufficient light homogeneity to the user to perform a light sensibility measurement. In this arrangement, the displaying and the optical units which enable to perform a visual acuity measurement are positioned behind the diffuser to allow the eyes of the user to face the diffuser without any visual obstacle between the diffuser and the eyes of the user. The device thus combines two high-precision measurement systems.

The device is preferably a wearable device. This wearable configuration of the device enables easy handling so that a light sensitivity threshold measurement and/or a visual acuity measurement may be performed quickly. Combining a precise measurement with easy and practical handling allows to consider new uses for the device. Indeed, said device may be used directly by the eye care professional without the need of a bulky measurement machine.

According to an embodiment of said device, said diffuser forms at least one window allowing said user to see said displaying unit through said optical unit and said at least one window.

According to an embodiment of said device, said displaying unit comprises a first and a second screens configured to respectively display at least one first image to a first eye of the user and at least one second image to a second eye of the user.

According to an embodiment of said device, said first and second screens have a screen size lower or equal to 40 mm.

According to an embodiment of said device, said at least one window comprises a first and a second windows each facing an eye area of the user when said device is worn by the user, said first window being aligned with said at least two first and said first screen, said second window being aligned with said at least two second lenses and said second screen.

According to an embodiment of said device, said optical unit is configured to provide an optical magnification lower than 1 to said optical unit According to an embodiment of said device, said optical unit comprises:

- at least two first lenses disposed between the displaying unit and a first eye of the user when the device is worn by the user, and
- at least two second lenses disposed between the displaying unit and a first eye of the user when the device is worn by the user.

According to an embodiment of said device, at least two first lenses are disposed within a first optical tube fixed to said first screen, said at least two second lenses are disposed within a second optical tube fixed to said second screen, said first and second optical tubes being respectively aligned with said first and second windows to allow the user to see said displaying unit through first and second optical tubes.

According to an embodiment of said device, said at least two first lenses and said at least two second lenses each comprise a converging lens and a divergent lens to provide an optical magnification lower than 1 to said optical unit.

According to an embodiment of said device, it further comprises a positioning system configured to move said at least two first lenses and said first screen with regard to said first window as well as said at least two second lenses and said second screen with regard to said second window to modulate the position of the optical and displaying units depending on a pupillary distance of a user.

According to an embodiment of said device, said sensing unit is configured to determine when said user recovers a predetermined visual acuity after said at least one eye of the user is stimulated by said at least one light source.

According to an embodiment of said device, it further comprises an imaging unit configured to take at least one image of at least one eye of the user.

According to an embodiment of said device, said at least one light source is configured to emit light toward said diffuser to indirectly stimulate said at least one eye of the user.

According to an embodiment of said device, said diffuser comprises predetermined parameters allowing to provide a homogeneous light diffusion to at least one eye of the user from light emitted by said at least one light source. According to an embodiment of said device, said predetermined parameters comprise at least one among: shape, geometry and material of the diffuser.

According to an embodiment of said device, said predetermined parameters allow to provide a light diffusion with a homogeneity of at least 55%, preferably at least 60%, preferably at least 70%, 80%, preferably of at least 90%, most preferably of at least 95%.

According to an embodiment of said device, the sensing unit comprises at least one switch reachable by the user to provide at least one signal representative of a visual acuity of the user.

According to an embodiment of said device, said optical unit comprises at least one lens comprising an adjustable power or being configured to move at least one lens to adjust the power of said at least one lens The invention further provides a method for determining a visual acuity of a user, comprising the following steps:

- providing a device, comprising:
  - a displaying unit configured to display at least one image to at least one eye of the user when the device is worn by the user,
  - an optical unit disposed between the displaying unit and at least one eye of the user when the device is worn by the user,
  - a diffuser disposed between said optical unit and at least one eye of the user when the device is worn by the user so that said diffuser faces at least one eye of the user,
  - at least one light source for stimulating at least one eye of the user,
  - a sensing unit configured to acquire at least one signal representative of a visual acuity of the user.
- positioning the device on the user's head such that said diffuser faces at least one eye of the user;
- displaying at least one image to at least one eye of the user through said optical unit to allow the user to see said at least one image,
- acquiring at least one signal representative of a visual acuity of the user;
- determining a parameter representative of a visual acuity of a user depending on said at least one signal representative of a visual acuity of the user.

According to an embodiment of said method, said at least one image is an optotype allowing to determine a visual acuity of said user, said optotype having a size lower or equal to 5/10 after being reduced through said optical unit.

According to an embodiment of said method, it further comprises, before the step of displaying said at least one image:

either:

- displaying at least one initial image to at least one eye of the user through said optical unit to allow the user to see said at least one image;
- acquiring at least one initial signal representative of a visual acuity of the user;
- determining an initial parameter representative of a visual acuity of a user depending on said at least one signal representative of a visual acuity of the user;
- stimulating at least one eye of the user with said at least one light source, wherein said step of determining a parameter representative of a visual acuity comprises determining when said user recovers a predetermined visual acuity after said at least one eye of the user is stimulated by said at least one light source, or stimulating at least one eye of the user with said at least one light source, wherein said step of determining a parameter representative of a visual acuity comprises determining the visual acuity of the user.

According to an embodiment of said method, said determining method is a computer-implemented method.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DETAILED DESCRIPTION OF EMBODIMENTS

Figure 1:
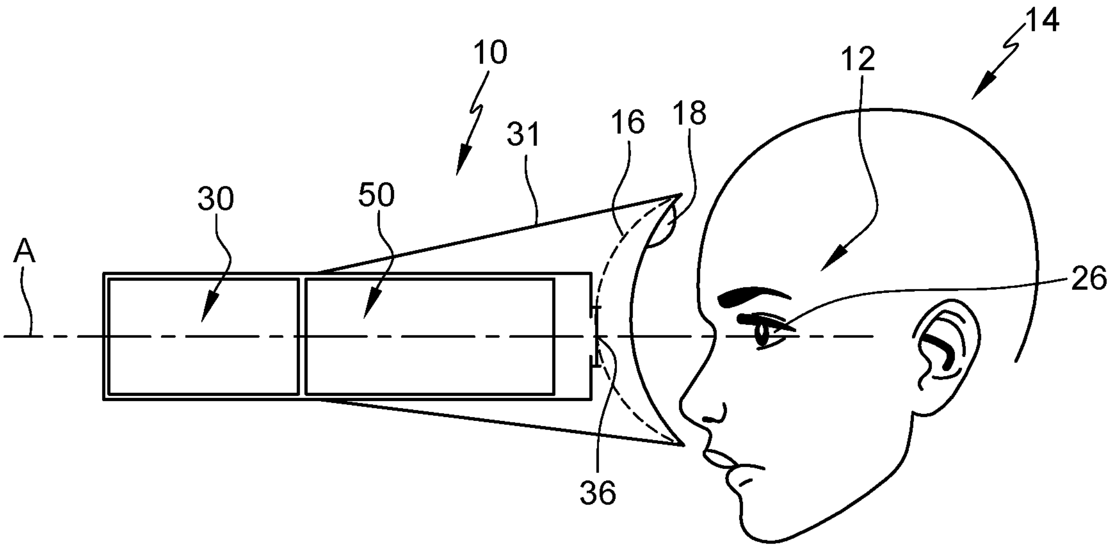
FIG. 1 schematically shows a side view of device for a parameter representative of a visual acuity of a user.

In the description which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may embodied in a wide variety of contexts. Embodiments discussed herein are merely representative and do not limit the scope of the invention. It will also be obvious to one skilled in the art that all the technical features that are defined relative to a process can be transposed, individually or in combination, to a device and conversely, all the technical features relative to a device can be transposed, individually or in combination, to a process.

The terms "comprise" (and any grammatical variation thereof, such as "comprises" and "comprising"), "have" (and any grammatical variation thereof, such as "has" and "having"), "contain" (and any grammatical variation thereof, such as "contains" and "containing"), and "include" (and any grammatical variation thereof such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises", "has", "contains", or "includes" one or more steps or elements possesses those one or more steps or elements but is not limited to possessing only those one or more steps or elements.

The present invention provides a wearable device for determining a parameter representative of a visual acuity. This device may be an eyewear device, for example a head mounted display.

As shown on FIG. 1, said device 10 may be a binocular device so that it is configured to face each eye area 12 of a user 14 in use. Alternatively, the device 10 may be monocular. In this latter case, the device may be configured to face only one eye area 12 of the user 14.

The wearable device 10 may be configured to be worn by a user 14. Preferably, the device 10 is configured to be positioned and supported onto the head of the user 14 to be able to face at least one eye area 12 of the user 14. In other words, dimensions and weight of the device 10 are configured to make it possible for a user 14 to handle it in front of its eyes using supporting means. Said supporting means may be its hands so that the user 14 handles the device 10 as binoculars. Alternatively, supporting means may be means for fastening the device 10 to the user's head as straps able to surround the user's head or spectacle arms positioned onto the user's ears. Alternatively, supporting means may be a support leg configured to sit on a table or on the ground. Furthermore, the device 10 may comprise an accumulator to be self-sufficient in energy.

By "a parameter representative of a visual acuity", what is meant is a parameter associated to visual acuity or a visual acuity measurement. For example, a parameter associated or representative to a visual acuity is a visual acuity recovery time of the subject after being exposed to a particular lighting environment or stimuli. Visual acuity is considered to be recovered when the user 14 is able to recognize a visual shape corresponding to a predetermined visual acuity. Said visual shape is preferably at least one optotype.

An "optotype" is a normalized drawing and/or character allowing to measure visual acuity. An example of such an optotype is a C-shaped optotype wherein the gap between the two ends of the C is randomly oriented in a given direction. In this measurement test, the user 14 has to determine the correct orientation of the optotype.

An eye area 12 comprises at least one among lower and upper eyelids, an eyebrow, an eyelash, an eye, the skin around the eye as well as muscle around the eye.

The device 10 is configured to determine a light sensitivity threshold of the user 14 by monitoring the response of the user's eye areas 12 when subjected to a given light environment.

By "sensitivity to light" of the user 14, what is meant is any relatively intense and prolonged reaction or modification of comfort or visual performance in relation to a temporary or continuous light flux or stimuli. The quantity representative of the sensitivity of the eye of the user 14 to said characteristic light flux is the light sensitivity threshold. It can be determined by measuring physical responses experienced by the user 14 or any action of the user 14 representative of its discomfort or visual perception. It allows the visual performance and/or visual discomfort experienced by the user 14 to be determined objectively.

Said device 10 also comprises a diffuser 16 and at least one light source 18 to emit light toward the diffuser 16. Said device 10 is thus configured to provide homogeneous light diffusion to one or two eyes of the user 14. Particularly, said diffuser 16 comprises predetermined parameters allowing to provide a quasi-homogeneous light diffusion to at least one eye of the user 14 from light emitted by said at least one light source 18.

The diffuser 16 is preferably chosen to act as a light reflector of light but as diffusive as possible. It requires both a satisfactory reflection efficiency (great albedo) to be optically efficient and the ability not to have a specular reflection so that the output light seems very uniform despite the diffuser is enlighten by punctual light sources 18.

Some materials naturally have said both abilities, such as barium sulfate or Titanium Dioxide ($TiO2$). It is also possible to have pigments or white dyes in the material forming the diffusing surface to have a satisfactory albedo. A surface treatment may also be performed to suppress specular reflection, as managing surface roughness (graining), or with one or more coatings acting as anti-glare.

Said diffuser 16 may comprise an internal surface having an albedo of at least 80%, preferably of at least 90%, most preferably of at least 95%. In other words, the internal surface of the diffuser 16 is chosen to reflect the maximum intensity of light emitted by the light source 18. Furthermore, said internal surface is preferably a diffusely reflecting surface. In other words, there is equal luminance when viewed from all directions lying in the half-space adjacent to the surface. For example, the internal surface of the diffuser 12 may comprise a coating made of barium sulfate to have a diffusely reflecting surface with an albedo of at least 80%.

By "quasi-homogeneous" or "homogeneous" light diffusion, we mean a light diffusion with a homogeneity of at least 55%, preferably at least 60%, preferably at least 70%, preferably at least 80%, preferably of at least 90%, most preferably of at least 95%.

Said predetermined parameters comprise at least one among: shape, geometry and material of the diffuser 16.

Such predetermined parameters of the diffuser 16 allow to obtain a quasi-homogeneity diffusion with lower energy consumption of the light source 18 with respect to known devices 10. It is particularly useful for a wearable device 10 that consequently needs batteries with reduced power energy.

Said at least one light source may be used for stimulating at least one eye of the user. Said at least one light source thus may be called a stimuli source which aims at inducing a variation of at one least one characteristic of the eye area. As an example, emitting light towards the eye of the wearer at a high luminance may induce a closure of the eyelid, contraction of muscles and a contraction of the pupil. This stimuli source is particularly useful when the behavior which is determined is a change in the visual comfort or performance, as glare.

Said at least one light source 18 may comprise at least one light-emitting diode (LED) disposed behind said diffuser 16. In this case, the at least one light source emits light directly toward one or both eyes of the user. For example, said at least one light source 18 may comprise at least one LED of a screen disposed behind the diffuser 16 to provide punctual light source.

Said at least one light source 18 may comprise at least one light-emitting diode (LED) disposed in front of said diffuser 16. In this case, the at least one light source emits light toward the diffuser 16 to provide a diffused light to the user. Said at least one light source 18 may be lodged in a cavity formed by a casing 31 of the device 10.

The device 10 may thus be configured to expose the user to either a homogeneous or punctual light, or both simultaneously.

Stimuli source preferably comprises at least one light-emitting diode (LED) able to have variable light spectrum as RGB LEDs (Red-Green-Blue light emitting diodes) or RGB-W LEDs ((Red-Green-Blue-White light emitting diodes). Alternatively, said stimuli source may be configured to provide a predetermined single white light spectrum or, alternatively, a spectrum having all visible radiations with substantially the same intensity, in contrast with a spectrum having peaks. Said at least one stimuli source is preferably controlled with a constant current to obtain a constant light flux coming out said at least one stimuli source. Providing the user with a constant light flux allows to reduce or avoid biological effects disturbances compared to stimuli sources controlled with Pulse Width Modulation (PWM).

Said stimuli source may be used to stimulate the user 14 before a visual acuity measurement. In other words, a visual acuity measurement may be performed after glare.

Figure 3:
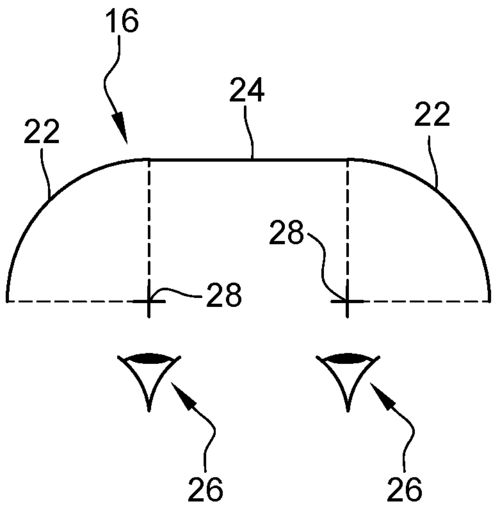
FIG. 3 schematically shows a top view of a diffuser of said device of FIGS. 1 and 2.

As shown on FIG. 3, said diffuser 16 is preferably concave. When said device 10 is binocular, said diffuser 16 comprises at least two concave portions 22 having respectively two centers of curvature 28 distinct from each other. At least one among said at least two concave portions 22 may be at least partially spherical. In this latter case, the centre of curvature 28 of said one among said at least two concave portions 22 being the centre of the sphere. Said diffuser 16 is preferably configured to dispose the centre of curvature of a concave portion between an eye 26 of the user 14 and said concave portion 22. Said concave portions 22 are preferably disposed on each side of a planar central portion 24.

Figure 2:
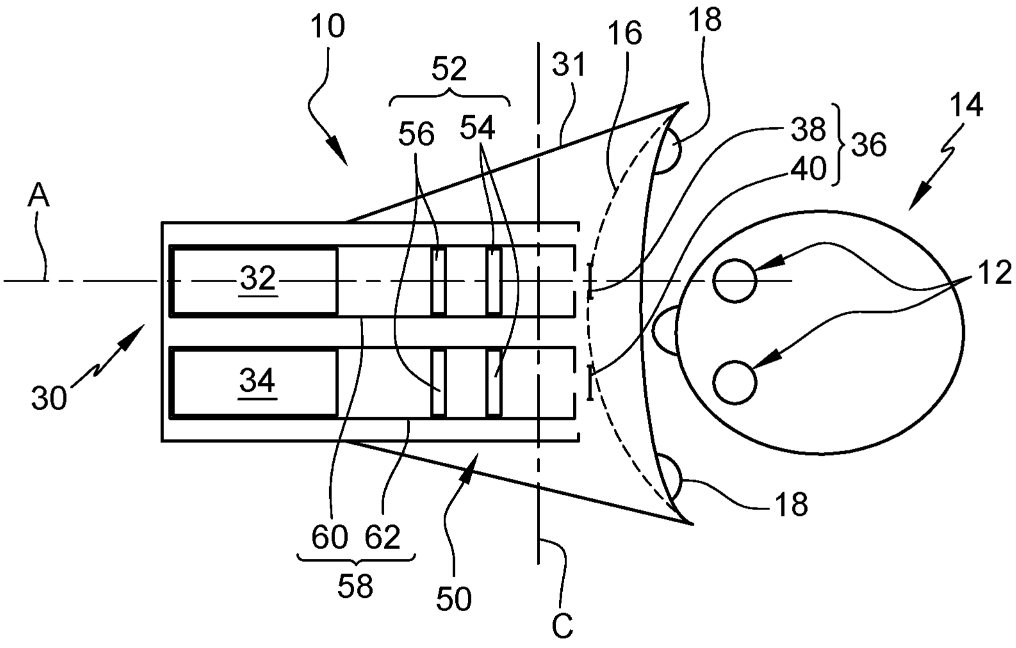
FIG. 2 schematically shows a top view of the device shown on FIG. 1.

Said device 10 further comprises a displaying unit 30 configured to display at least one image to at least one eye of the user 14 when the device 10 is worn by the user 14. Said displaying unit 30 is configured to display at least one optotype. Said displaying unit 30 is for example a screen. When the device 10 is binocular, said displaying unit 30 comprises at least two screens to display at least one image to both eyes of the user 14. As shown on FIG. 2, said device 10 preferably comprises a right 32 and a left 34 screen respectively configured to provide an image to a right and a left eyes of the user 14.

Said screen preferably has a screen size lower or equal to 40 mm to limit the dimensions of the wearable device 10.

Said screen can also constitute the stimuli light source by itself. The average luminance of the image displayed on the screens (optotypes and background) is in this case controlled to define the chosen lighting condition (darkness, twilight, daylight . . . ) and the lighting environment of the subject outside of the wearable device is also adapted (light turned on in a room and/or use of an opaque mask disposed between the subject's face around his/her eyes, and the diffuser to avoid any light but the one produced by the displaying unit, to reach the subject's eyes). The parameter representative of a visual acuity can be the visual acuity recovering time of the subject after being exposed to a daylight lighting environment and put into twilight/darkness during a predetermined period, or can be the visual acuity of the subject during his/her exposure to twilight/darkness lighting environment.

Said at least one image displayed by said right 32 and left 34 screens may be either identical or different. In this latter case, stereoscopic images may be displayed to the user to allow him to perceive a tridimensional image. Different images may also be displayed to adjust the pupillary distance of the user, e.g. by displaying a circle on one screen and a target on the other screen and asking the user to visually gather thereof.

Figure 4:
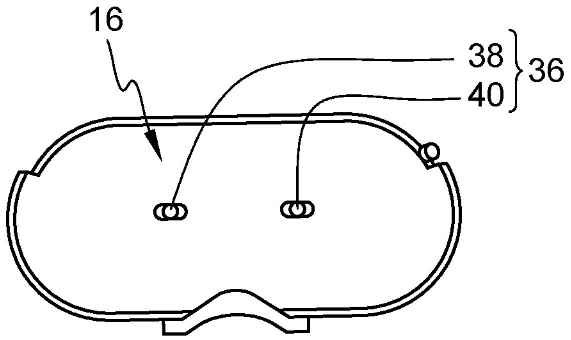
FIG. 4 schematically shows a front view of said diffuser of FIG. 3.

As shown on FIG. 4, the user 14 is able to see said displaying unit 30 through at least one window 36 formed by said diffuser 16. In a binocular arrangement said diffuser 16 forms at least two windows 36, e.g. a right 38 and a left 40 windows. Said at least one window 36 may be an empty window, i.e. an aperture formed into the surface of the diffuser 16, or a solid window, i.e. a window formed by a wall portion formed by the diffuser 16. A solid window is preferably at least partially transparent to allow the user to see the image through said window 36.

Said solid window may be obtained by using a transparent diffuser 16 which is only partially recovered by a coating, i.e. not at the window area. In doing so, the diffuser is transparent at the window and able to diffuse light emitted by said the stimuli source only where it is recovered by said coating.

Another solution to provide a solid window is to provide a transparent diffuser 16 totally recovered by a holographic filter configured to only reflect light emitted by the stimuli source. In other words, the holographic filter is able to reflect and thus provide a diffused light only for a predetermined range of wavelengths, chosen to correspond to the stimuli source. The images provided by the displaying unit does not correspond to the predetermined range of wavelengths such that said images may be seen by the user through the diffuser 16. To allow a simultaneous stimulus of the user while displaying at least one image by the displaying unit 30, the holographic filter may recover all the surface of the diffuser 16 but the window area. In doing so, the user is always able to see through the window.

Each of said windows 36 faces an eye area 12 of the user 14 when said device 10 is worn by the user 14. Said windows are preferably aligned with said displaying unit 30 to allow a user 14 to directly look at the image displayed by the displaying unit 30.

Alternatively, a wave guide may be disposed between the displaying unit 30 and said window 36 to be able to transport the image displayed by the displaying unit 30 in a position where the user 14 is able to look at it. Said wave guide is for example at least one mirror or at least one optical fiber. The user 14 is here able to look at said image in an indirect manner.

Said device 10 further comprises an optical unit 50 disposed between the displaying unit 30 and at least one eye 26 of the user 14 when the device 10 is worn by the user 14. Said optical unit 50 is preferably configured to provide an optical magnification lower than 1 to said optical unit. In other words, the optical unit 50 is preferably configured to deliver to the user 14 from the image displayed by the displaying unit, an image seen at far distance (more than 4 to 6 meters of observation) and with a reduced size but with a higher resolution. This resolution corresponds to the predetermined visual acuity which is required by the resolution of the optotype chosen for the measurement test (e.g. 5/10). Said optical unit 50 allows to provide an image with a high resolution while using a cost effective and small screen.

Said magnification lower than 1 is obtained preferably using at least two lenses 52. Said at least two lenses are aligned with said displaying unit 30, with a same screen of the displaying unit 30. Hence, when the device 10 is monocular, said displaying unit 30 may comprise a single screen aligned with at least lenses 52 which are positioned between said screen and an eye of the user 14 when the device 10 is worn by said user 14. When the device 10 is binocular, said displaying unit may comprise said right 32 and left 34 screens aligned with two sets of at least two lenses 52 which are positioned between one of said screens and an eye of the user 14 when the device 10 is worn by said user 14. In other words, said user 14 looks at the image displayed by a screen of the displaying unit 30 through at least two lenses 52.

Said at least two lenses 52 comprises a converging lens 54 and a divergent lens 56 to provide an optical magnification lower than 1 to said optical unit. Particularly, said divergent lens 56 is disposed between said displaying unit 30 and the diffuser 16. Said convergent lens 54 is disposed between said diffuser 16 and said divergent lens 56.

Figure 5:
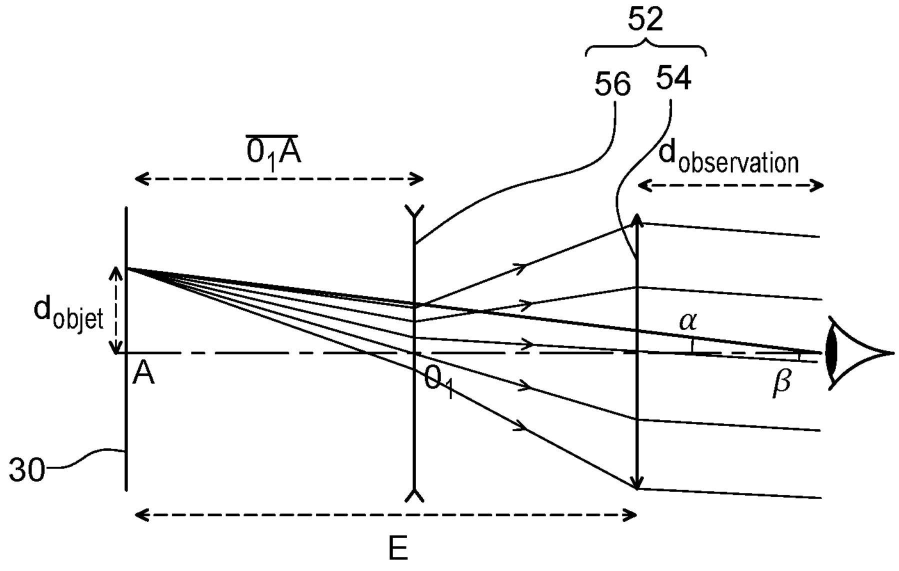
FIG. 5 shows a graphic representation of an optical unit of said device of FIGS. 1 and 2.

Distance between said divergent lens 56 and said displaying unit 30, as well as distance between said convergent lens 54 and said displaying unit 30, are determined to minimize the bulkiness of the device 10 while maintaining the predetermined resolution of the image and make it observed at far distance by the subject. A solver may be used on the basis of these three equations, in reference to FIG. 5:

$$E = f'conv - \frac{O1A^2}{f'div + O1A}$$

$$\beta = \frac{dobjet * \gamma t}{f'conv}$$

-continued $$\gamma t = \frac{f'div}{f'div + O1A}$$

With

E which is the distance between the screen and the convergent lens f'conv which is the focal length of the convergent lens O1A which is the distance between the displaying unit 30 and the divergent lens f'div which is the focal length of the divergent lens β which is the output angle dobjet which is the distance between a point of the displaying unit 30 and the optical axis γt which is the magnification of the system Each set of at least two lenses 52 is also preferably aligned with a window 36. In a binocular configuration, right window 38 is aligned with at least two lenses 52 and said right screen 32. In the same way, left window 40 is aligned with at least two lenses 52 and said left screen 34.

According to another embodiment, the at least two lenses can comprise or can be associated to one or a plurality of lenses with adjustable power, such as liquid lenses, or as a more specific example a visual compensation system as described in document WO 2015/155 458.

For example, said at least two lenses can include a lens having a variable spherical power.

Said variable spherical power lens has for instance a deformable surface. The shape of this surface (in particular the radius of curvature of this surface, and hence the spherical power provided by the lens) can be controlled by moving a mechanical part (such as a ring), which mechanical part may be driven by a motor.

Said at least two lenses can include a pair of independently rotatable lenses each having a cylindrical power.

They may each be rotated by action of other motors.

The motors are controlled by a control unit such that the combination of the variable spherical power lens and the two cylindrical power lenses provides a desired spherical correction and a desired cylindrical correction to the individual's eye, as explained in document WO 2015/107 303.

The variable spherical power lens, the cylindrical lenses, the motors and the control unit) are enclosed in a small module housing 12 constituting a visual compensation system.

In the present embodiment of the device according to the invention, it includes two visual compensation systems as mentioned above, each such system being dedicated to one of the individual's eyes. The adjustable powers of these visual compensation systems are vision correction powers for the eye of the individual placed nearby.

Said optical unit 50 may comprise a modulation system configured to move one or more of said at least two lenses 52 with each other, and/or with regard to the displaying unit 30, to modulate the magnification of the displayed image and/or the distance of observation of the displayed image by the subject and/or the visual correction brought to the subject.

Figure 6:
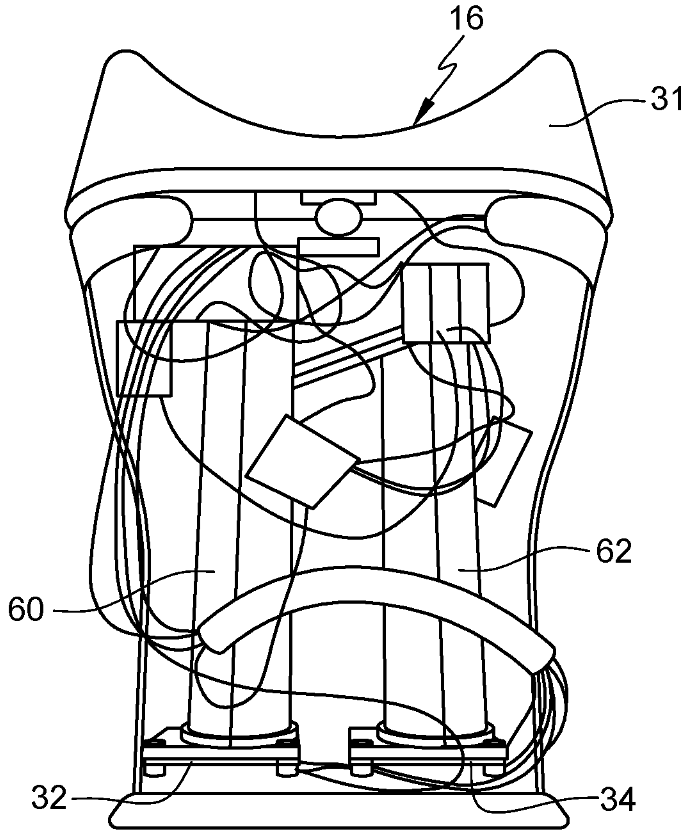
FIG. 6 schematically shows a top view of an embodiment of the device of FIGS. 1 and 2 with an upper casing which is removed.

As shown on FIG. 6, said optical unit 50 comprises at least one optical tube 58 receiving said at least two lenses 52. Said at least optical tube 58 has a first open end facing said displaying unit 30 and a second open end, opposite the first open end, facing a window 3 or a wave guide. The user 14 thus sees said displaying unit 30 through said at least one optical tube 58.

In a binocular configuration, said optical unit 50 comprises a right optical tube 60 disposed between the right screen 32 and said right window 38. Said optical unit 50 further comprises a left optical tube 62 disposed between the left screen 34 and said left window 40.

Said at least one optical tube 58 is preferably fixed to the displaying unit 30 to make the optical unit 50 fixed or secured to the displaying unit 30. In doing so, it is possible to move the optical unit 50 and the displaying unit 30 altogether. This is particularly useful when setting the device 10 with regard to the pupillary distance of a user 14, in a binocular configuration.

Said at least one window 36 is preferably not fixed to the optical unit 50 so that a move of the optical 50 and displaying 30 units does not cause a movement of the window 36.

Figure 7:
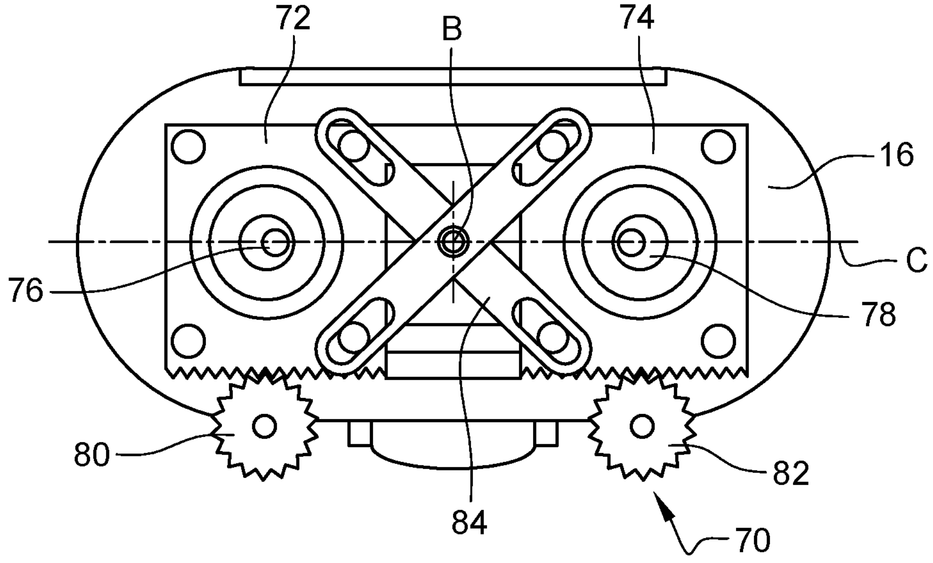
FIG. 7 schematically shows a positioning system of the device of FIGS. 1 and 2.

As shown on FIG. 7, said device 10 may further comprise a positioning system 70 when the device 10 is in a binocular configuration. Said positioning system 70 is configured to move said optical 50 and displaying 30 units with regard to the diffuser 16, and so with regard to the user's face when the device 14 is worn. Indeed, said diffuser 16 is fixed on the face of the user 14 when the device 10 is worn. Said positioning system 70 thus allows to position the image displayed by the displaying unit 30 and reduced by the optical unit 50 with regard to the eyes 26 of the user 14.

Said positioning system 70 is preferably configured to modulate the position of the optical 50 and displaying 30 units depending on a pupillary distance of a user 14. To that end, said positing system 70 allows to move the optical 50 and displaying 30 units in a direction C perpendicular to the sagittal plan when considering an orthonomic reference frame of the user 14. This direction C may also be characterized as being perpendicular to an axis A passing through a window 36 and the eye 26 of the user 14.

For a precise positioning of the optical 50 and displaying 30 units, said positioning system 70 is preferably configured to move each right and left portions the optical 50 and displaying 30 units simultaneously. In other words, said positioning system 70 is configured to simultaneously translate said right optical tube 60 fixed to the right screen 32 and said left optical tube 62 fixed to the left screen 34 by a same distance. In doing so, it is possible to adapt the distance between right and left portions the optical 50 and displaying 30 units to fit the pupillary distance of the user 14 in a single movement.

An embodiment of such a positioning system 7 using a simultaneous translation is shown on FIG. 7. Said positioning system 70 comprises a right 72 and a left 74 carriages respectively defining a right 76 and a left 78 orifices. Said right 60 and left 62 optical tubes are respectively fixed to said right 72 and a left 74 carriages, facing said right 76 and left 78 orifices. Said right 76 and a left 78 orifices are positioned to respectively face the right 38 and left 40 windows so that the user 14 is able to see through said right 76 and left 78 orifices when looking at the displaying unit 30.

Said right 72 and left 74 carriages are mounted to be able to freely translate along said direction C perpendicular to the sagittal plan. Said positioning system 70 also comprises a right 80 and left 82 driving wheels configured to translate said right 72 and left 74 carriages in opposite directions along said direction C perpendicular to the sagittal plan.

Said positioning system 70 further comprises a double arm organ 84 able to link the translation movement of each of said right 72 and left carriages 74. Said double arm organ 84 is arranged in a cross-shaped configuration wherein each arm is able to rotate which each other around a central axis B perpendicular to a frontal plan of the user 14. Each arm of said double arm organ 84 is attached both right 72 and left carriages 74 to link the translation thereof. Particularly, each of said right 72 and left carriages 74 comprises a relief able to be guided by a corresponding relief formed by an arm of said double arm organ 84. One of these relief may be a rod and the corresponding relief may be a recess allowing the rod to be guided thereto.

Said device 10 may also comprise an imaging unit configured to take at least one image of at least one eye 26 of the user 14. Said imaging unit is for example at least one video camera. Said imaging unit may be configured to perform photorefraction to enhance the visual acuity measurement. Said imaging unit may be disposed behind said diffuser 16 (on the optical unit side of the diffuser) and to face at least one eye of the user 14 behind the window. Said imaging unit may be configured to take said at least one image through a solid or empty window formed by the diffuser 16.

Said device 10 further comprises a sensing unit configured to acquire at least one signal representative of a visual acuity of the user 14. Said sensing unit may comprise at least one switch reachable by the user 14 on the periphery of the device 10. This at least one switch allows the user to communicate with the device 10, for example by transmitting information representative of its light sensitivity and/or information regarding visual acuity. In a preferred embodiment, at least one switch is configured to allow the user to indicate the orientation of the image displayed by the displaying unit 30.

This sensing unit may also comprise controlling means configured to provide at least one among: controlling the luminance of light emitted by said at least one light source 18, controlling the duration of the light emission, spatial repartition of the light emission, the spectrum of the light emission, the displaying unit 30 and the optical unit 50. Said controlling means may be inserted in the casing 31, for example behind the diffuser 16.

Furthermore, said device 10 preferably comprises one or more battery configured to supply the at least one light source 18, the displaying unit 30, the optical unit 50 and the sensing unit with electrical energy. Said device 10 may further comprise communication means configured to transmit information to an external module and/or to receive information from this external module. Said module may be a smartphone or a computer.

A visual acuity measurement may be performed as follows using a first method for determining when a user recovers a predetermined visual acuity after a light stimulus and a second method for determining the visual acuity of a user after a light stimulus.

Said first method regarding vision recovery is described below.

The device 10 is positioned on the user's head such that said diffuser 16 faces at least one eye of the user 14. At least one initial image is displayed to at least one eye of the user 14 through said optical unit 50 to allow the user 14 to see said at least one initial image. Said initial image has a resolution corresponding to a visual acuity recovering test, preferably lower or equal to 5/10.

At least one initial signal representative of a visual acuity of the user is then acquired.

An initial parameter representative of a visual acuity of a user is then determined depending on said at least one initial signal representative of a visual acuity of the user.

Displaying said at least one initial image allows to perform a reference test of visual acuity before any exposure to light from the light source 18.

Then, at least one eye of the user is stimulated with said at least one light source 18. This stimulus may provide glare.

At least one image is displayed to at least one eye of the user 14 through said optical unit 50 to allow the user 14 to see said at least one image. Said image has a resolution corresponding to a visual acuity recovering test, preferably lower or equal to 5/10.

At least one initial signal representative of a visual acuity of the user is then acquired. A final parameter representative of a visual acuity of a user is then determined depending on said at least one signal representative of a visual acuity of the user. Said final parameter refers to when said user recovers a predetermined visual acuity after said at least one eye of the user is stimulated by said at least one light source.

Before the step of displaying said at least one image, at least one eye of the user may be stimulated with said at least one light source 18 via the diffuser or via the screens. In this case, said step of determining a parameter representative of a visual acuity comprises determining when said user recovers a predetermined visual acuity after said at least one eye of the user is stimulated by said at least one light source.

Said second method regarding a visual acuity test is described below.

The device 10 is positioned on the user's head such that said diffuser 16 faces at least one eye of the user 14.

An optional step of stimulating at least one eye of the user may be performed with said at least one light source 18 via the diffuser 16 or via the screens. In doing so, the user may be provided with a specific light environment which may reproduce some predetermined situations: e.g. dark light, twilight, night vision). Alternatively or in combination, this stimulation may expose the user to glare.

At least one image is displayed to at least one eye of the user 14 through said optical unit 50 to allow the user 14 to see said at least one image. Said image has a resolution corresponding to a visual acuity test, preferably greater or equal to 10/10, most preferably greater or equal to 15/10.

At least one signal representative of a visual acuity of the user is then acquired.

A parameter representative of a visual acuity of a user is then determined depending on said at least one signal representative of a visual acuity of the user.

This optional stimulating step may be performed before or during the following steps of the second method to allow the visual acuity test to be performed with a predetermined light environment.

During the light stimulation of the first and second methods, different levels of light intensity may be provided to the eyes of the user.

When the user is exposed to glare, at the beginning of the test, the light intensity is very low, and is progressively increased to measure the sensitivity threshold of the patient.

A preferred sequence of light stimulation is described below to expose the user to glare.

A continuous light emission may be provided to induce an illuminance from a minimum to a maximum values increasing the illuminance by stages, e.g. from 25 Lux to 10211 Lux. For example, the light emission may start with an illuminance of 25 Lux for 5 seconds to adapt the eye to the light condition and cancel all previous light exposure before the measurement and then continue with an increase of the illuminance of 20% each second to the maximum illuminance. In a more general way, the light may be emitted to induce an illuminance varying from 25 Lux to 10000 Lux. This continuous light emission may be performed with warm light. Another continuous light emission may be performed with cold light.

Then, a flashing light emission is performed to induce an illuminance from a minimum value to a maximum value increasing the illuminance by stages, e.g. from 25 Lux to 8509 Lux. The illuminance of the flashing light emission is preferably increased by at least 30%, preferably by 40%, most preferably by at least 44%. Before and between each flashlight emission, the user is subjected to a light emission lower than the minimum value of illuminance of the flashing light emission, e.g. 10 Lux. The time of each flashing light emission is preferably 0.5 s and the time between each flashing light emission is preferably 2 s.

The method according to the invention and performed by the device 10 is computer-implemented. Namely, a computer program product comprises one or more sequences of instructions that are accessible to a processor and that, when executed by the processor, cause the processor to carry out steps of the method for determining a visual acuity of a user as described above.

The sequence(s) of instructions may be stored in one or several computer-readable storage medium/media, including a predetermined location in a cloud.

Although representative methods and devices have been described in detail herein, those skilled in the art will recognize that various substitutions and modifications may be made without departing from the scope of what is described and defined by the appended claims.

The invention claimed is:

1. A wearable device for determining a parameter representative of a visual acuity of a user, comprising:

a displaying unit configured to display at least one image to at least one eye of the user when the device is worn by the user;

an optical unit disposed between the displaying unit and at least one eye of the user when the device is worn by the user;

a diffuser disposed between said optical unit and at least one eye of the user when the device is worn by the user so that said diffuser faces at least one eye of the user;

at least one light source for stimulating at least one eye of the user;

means allowing said user to see said displaying unit through said optical unit despite the disposition of the diffuser between said optical unit and at least one eye of the user when the device is worn by the user; and a sensing unit configured to acquire at least one signal representative of a visual acuity of the user, wherein said diffuser forms at least one window allowing said user to see said displaying unit through said optical unit and said at least one window, said window forming said means allowing said user to see said displaying unit through said optical unit.

2. The device according to claim 1, wherein said displaying unit comprises first and second screens configured to respectively display at least one first image to a first eye of the user and at least one second image to a second eye of the user.

3. The device according to claim 2, wherein said first and second screens have a screen size lower or equal to 40 mm.

4. The device according to claim 2, wherein said at least one window comprises first and a second windows each facing an eye area of the user when said device is worn by the user, said first window being aligned with said at least two first and said first screen, said second window being aligned with at least two second lenses and said second screen.

5. The device according to claim 1, wherein said optical unit is configured to provide an optical magnification lower than 1 to said optical unit.

6. The device according to claim 4, wherein said optical unit comprises:

at least two first lenses disposed between the displaying unit and a first eye of the user when the device is worn by the user, and at least two second lenses disposed between the displaying unit and a first eye of the user when the device is worn by the user.

7. The device according to claim 6, wherein at least two first lenses are disposed within a first optical tube fixed to said first screen, said at least two second lenses are disposed within a second optical tube fixed to said second screen, said first and second optical tubes being respectively aligned with said first and second windows to allow the user to see said displaying unit through first and second optical tubes.

8. The device according to claim 6, wherein said at least two first lenses and said at least two second lenses each comprise a converging lens and a divergent lens to provide an optical magnification lower than 1 to said optical unit.

9. The device according to claim 6, further comprising a positioning system configured to move said at least two first lenses and said first screen with regard to said first window as well as said at least two second lenses and said second screen with regard to said second window to modulate the position of the optical and displaying units depending on a pupillary distance of a user.

10. The device according to claim 1, wherein said sensing unit is configured to determine when said user recovers a predetermined visual acuity after said at least one eye of the user is stimulated by said at least one light source.

11. The device according to claim 1, further comprising an imaging unit configured to take at least one image of at least one eye of the user.

12. The device according to claim 1, wherein said optical unit comprises at least one lens comprising an adjustable power or being configured to move at least one lens to adjust the power of said at least one lens.

13. A method for determining a visual acuity of a user, comprising the following steps:

providing a device, comprising:

a displaying unit configured to display at least one image to at least one eye of the user when the device is worn by the user, an optical unit disposed between the displaying unit and at least one eye of the user when the device is worn by the user, a diffuser disposed between said optical unit and at least one eye of the user when the device is worn by the user so that said diffuser faces at least one eye of the user, at least one light source for stimulating at least one eye of the user, means allowing said user to see said displaying unit through said optical unit despite the disposition of the diffuser between said optical unit and at least one eye of the user when the device is worn by the user, and a sensing unit configured to acquire at least one signal representative of a visual acuity of the user, wherein said diffuser forms at least one window allowing said user to see said displaying unit through said optical unit and said at least one window, said window forming said means allowing said user to see said displaying unit through said optical unit;

positioning the device on the user's head such that said diffuser faces at least one eye of the user;

displaying at least one image to at least one eye of the user through said optical unit to allow the user to see said at least one image;

acquiring at least one signal representative of a visual acuity of the user; and determining a parameter representative of a visual acuity of a user depending on said at least one signal representative of a visual acuity of the user.

14. The method according to claim 13, further comprising, before the step of displaying said at least one image: either:

displaying at least one initial image to at least one eye of the user through said optical unit to allow the user to see said at least one image;

acquiring at least one initial signal representative of a visual acuity of the user;

determining an initial parameter representative of a visual acuity of a user depending on said at least one signal representative of a visual acuity of the user;

stimulating at least one eye of the user with said at least one light source, wherein said step of determining a parameter representative of a visual acuity comprises determining when said user recovers a predetermined visual acuity after said at least one eye of the user is stimulated by said at least one light source, or stimulating at least one eye of the user with said at least one light source, wherein said step of determining a parameter representative of a visual acuity comprises determining the visual acuity of the user.

15. The method according to claim 13, wherein the method is a computer-implemented method.

16. The device according to claim 1, wherein said displaying unit comprises first and second screens configured to respectively display at least one first image to a first eye of the user and at least one second image to a second eye of the user.

17. The device according to claim 3, wherein said at least one window comprises first and second windows each facing an eye area of the user when said device is worn by the user, said first window being aligned with said at least two first and said first screen, said second window being aligned with at least two second lenses and said second screen.

18. The device according to claim 4, wherein said optical unit is configured to provide an optical magnification lower than 1 to said optical unit.

19. The device according to claim 5, wherein said optical unit comprises:

at least two first lenses disposed between the displaying unit and a first eye of the user when the device is worn by the user, and at least two second lenses disposed between the displaying unit and a first eye of the user when the device is worn by the user.

* * * * *